(12) United States Patent
Lischka et al.

(10) Patent No.: US 7,116,754 B2
(45) Date of Patent: Oct. 3, 2006

(54) DIFFRACTOMETER

(75) Inventors: Klaus Lischka, Paderborn (DE); Alexander Kharchenko, Almelo (NL)

(73) Assignee: PANalytical B.V., Almelo (NL)

( * ) Notice: Subject to any disclaimer, the term of this patent is extended or adjusted under 35 U.S.C. 154(b) by 0 days.

(21) Appl. No.: 11/065,715

(22) Filed: Feb. 24, 2005

(65) Prior Publication Data
US 2005/0195941 A1   Sep. 8, 2005

(30) Foreign Application Priority Data
Mar. 1, 2004   (EP)   ................................. 04251181

(51) Int. Cl.
*G01N 23/10* (2006.01)

(52) U.S. Cl. .......................................... 378/79; 378/73
(58) Field of Classification Search .................... 378/9, 378/71, 73, 74, 79, 80, 82, 84, 70, 81; 117/201
See application file for complete search history.

(56) References Cited

U.S. PATENT DOCUMENTS

| | | | |
|---|---|---|---|
| 4,274,000 A * | 6/1981 | Goebel .......................... | 378/75 |
| 5,636,258 A * | 6/1997 | Okumura et al. .............. | 378/73 |
| 5,923,720 A | 7/1999 | Barton et al. | |
| 6,421,414 B1 * | 7/2002 | Huber .......................... | 378/45 |
| 6,882,739 B1 * | 4/2005 | Kurtz et al. .................. | 382/109 |
| 2001/0043668 A1 * | 11/2001 | Hayashi et al. ............... | 378/89 |
| 2002/0097837 A1 * | 7/2002 | Fanton et al. .................. | 378/82 |

FOREIGN PATENT DOCUMENTS

DE   10346433 A1 *   5/2005
JP   20002 234793   8/2002

OTHER PUBLICATIONS

Niggemeier et al., "X-Ray Reflectometer of the Diagnostics of Thin Films During Growth", J. Appl. Cyrst. (1997) 30, pp. 905-908.
Bader A S et al, "Real-Time I N Situ X-Ray Diffraction as a Method to Control Epitaxial Growth" Applied Physics Letters, vol. 82, No. 26, Jun. 30, 2003, pp. 4684-4686.
Malhotra A K et al, "In situ/ex situ X-ray analysis system for thin sputteredfilms" Surf Coat Techn0l; Surface & Coatings Technology Nov. 10, 1998, vol. 110, No. 1-2, Nov. 10, 1998, pp. 105-110.
J. F. Whitacre et al, "Real -time/in situ diffr action study o f phase and microstructural ev o l u t i o n i n sputtered beta-Ta/Ta205 films" J. Vac. Sci. Technol. A, vol. 19, No. 6, Nov. 2001-Dec. 2001, pp. 2910-2919.
Kenji Ishida et al,: "Structural Evaluation of Epitaxially Grown Organic Evaporated Films by Total Reflection X-Ray Diffractometer" Journal of Applied Physics, vol. 73, No. 11, Jun. 1, 1993, pp. 7338-7343.
Luken E et al, "Growth monitoring of W/Si X-ray mu l ti layers by X-ray r e f l e c t i v i t y and kinetic ellipsometry" Proceedings of the SPIE, vol. 2253, Jun. 6, 1994, pp. 324-332.

* cited by examiner

*Primary Examiner*—Edward J. Glick
*Assistant Examiner*—Anastasia S. Midkiff
(74) *Attorney, Agent, or Firm*—Bromberg & Sunstein LLP

(57) ABSTRACT

A monochromator 4 is used to direct X-rays from X-ray source 2 onto a sample 14 as a convergent beam. The sample 14 is in a growth chamber. The sample is rotated, and diffraction measurements are made in parallel with multichannel detector 22. A specific reflection is used so that the intensity against angle graph measured in the multichannel detector gives information about the vertical lattice parameter. To compensate for wobble inevitably introduced by the rotation of the sample, short time measurements are made and summed.

13 Claims, 5 Drawing Sheets

DIFFRACTOMETER

CROSS REFERENCE TO RELATED APPLICATIONS

This application claims priority from European Patent Application Ser. No. 04251181.6, entitled "Diffractometer," filed on Mar. 1, 2004, which is hereby incorporated by reference, in its entirety.

TECHNICAL FIELD

The invention relates to a diffractometer and in particular to a diffractometer suitable for incorporation into a growth chamber, for example of a Metal-Organic Chemical Vapour Deposition (MOCVD) reactor, as well as to a growth chamber with the diffractometer installed, and methods of operating the diffractometer and processing data from the diffractometer.

BACKGROUND ART

MOCVD is a widely used process for depositing semiconductors and other materials in a growth chamber. It is very useful to monitor the growth of material in the growth chamber, and X-ray diffraction is a promising tool for this. There is also a need for monitoring growth in other types of growth chamber.

However, the construction of growth chambers leads to problems for X-ray diffractometers in that their construction necessarily needs to be optimised for growth and not for X-ray diffractometry.

Conventional X-ray diffraction approaches use a goniometer to orient incident and diffracted X-ray beams, but goniometers are difficult to use during growth and generally require a specially designed growth chamber.

Niggemeier et al, "X-Ray Reflectometer for the Diagnostics of Thin Films During Growth", J. App. Cryst. (1997), Vol. 30, pages 905 to 908, described a reflectometer for use with a sample stage in a growth chamber in which a line X-ray source is used to illuminate a curved-crystal monochromator, known as a curved-crystal monochromator, which directs X-rays through a window in the growth chamber onto a sample stage at a glancing angle. The X-rays are diffracted by the crystal and the X-rays diffracted at a glancing angle pass out to an X-ray detector through another window.

A similar, though somewhat later approach, is described in U.S. 2001/0043668 to Hayashi et al.

However, when a sample is mounted in a growth chamber, it is normally mounted on a rotating stage which will inevitably wobble somewhat, especially since excessive time taken to align the sample and axis of rotation would be prohibitive in a production environment. There is accordingly a need for a system that can cope with this wobble and accordingly take measurements during growth.

There is a further need for a system that can work quickly to enable results to be immediately available to allow the growth to be controlled on the basis of the measurements made.

SUMMARY OF THE INVENTION

According to one aspect of the invention there is provided an X-ray diffraction system for a system having a rotating sample stage. The system includes an X-ray source for emitting X-rays. A Johansson monochromator directs the X-rays emitted by the X-ray source as a convergent monochromatic beam defining a range of convergent incident angles onto a rotating sample stage in a deposition system. A multichannel X-ray detector is arranged to make a plurality of sets of measurements of intensity with a short measurement time $t_m$, each set of measurements of intensity being a set of measurements of intensity of X-rays diffracted by the sample at a plurality of diffraction angles, for making measurements of intensity with a measurement time $t_m$ given by $$t_m < \frac{t_r}{4}$$

where $t_r$ is the rotation period of the sample stage. A measurement system combines a plurality of the sets of measurements of intensity against diffraction angle by identifying the maximum in each set of measurements, and summing the sets of measurements together with the maxima aligned.

By summing together the plurality of measurements the diffractometer can cope with samples that are wobbling because they are rotating, and hence with features at different absolute angles in different measurements. The system is accordingly particularly suitable for monitoring growth in a deposition system, in particular a growth chamber.

In the case where the sample has a rotation time of $t_r$ and is used to measure a reflection that has n symmetric reflections in one rotation of the sample, the measurement time for each of the plurality of measurements $t_m$ is preferably given by:

$$t_m < \frac{t_r}{n}.$$

This is so that only one of the reflections in k-space as the sample is rotated contributes to each measurement.

The number of symmetric points around one full rotation depends on the material to be investigated as well as on the chosen reflection. For wurtzite type crystals like GaN, n is 6 for reflections (hkil) where h=k and n=12 for reflections where h≠k. For crystals with cubic symmetry: n is 4 for reflections (hkl) where h=k and n=8 for reflections where h≠k.

The measurement time for each set of measurements is in general short, i.e. less than 1 minute, and in most cases will need to be much shorter than this. Since typical rotation timescales are so short, of order 1 s, the measurements may need to be made over a time less than 1 s, and typically less than 0.5 s, often less than 0.3 s or even 0.2 s. Such measurement times are much shorter than those conventionally used. Measurements over such short timescales are not generally practical since the number of counts received by the X-ray detector is very small and normally insufficient to correctly characterise a diffraction pattern, which will accordingly seem very noisy. The inventors have realised that although measurements over such very short timescales are in general noisy the peak is still identifiable and can be used to align multiple short measurements so that they can be summed together.

X-ray diffraction apparatus as sold may include fixing means for attaching the diffraction apparatus to a growth chamber. Accordingly, the invention may further relate to the diffraction apparatus attached to the growth chamber, and hence including a growth chamber; a rotating sample stage in the growth chamber; a first X-ray window in the growth chamber arranged to pass incident X-rays from the Johansson monochromator to the sample stage; a second X-ray window in the growth chamber arranged to pass diffracted X-rays from the sample stage to the multichannel X-ray detector. The invention also relates to the apparatus with a sample mounted on the sample stage.

In a particularly preferred arrangement the incident angle is greater than 45° and the diffraction angle less than 30°.

The inventors have realised that by selecting a suitable reflection to carry out the measurements on it is possible to measure a single parameter and have this give directly a value for the vertical lattice parameter of the structure deposited on the structure without needing to measure two parameters to find the lattice parameters both vertically and horizontally. This allows the vertical lattice parameter to be quickly determined.

In the prior art paper by Niggemeier et al, this was not done and the measurements made there accordingly require the use of a slit to carry out a two-dimensional scan to give enough information. Accordingly, the prior art cannot carry out the measurements in situ nearly as quickly as that set out in the present invention making the prior art much less useful in practical growth chambers. Alternatively, in U.S. 2001/0043668, an alternative largely conventional rocking curve arrangement is used to take the scans as a function of angle where more information than simple film thickness is required, but this again takes more time.

The monochromatic convergent beam is represented by an arc in k-space and accordingly for each measured diffraction angle of X-rays diffracted by the sample the measured X-ray intensity will depend on the integral of the intensities in k-space over an arc determined by subtracting from the vector representing the diffracted X-rays the set of vectors representing the arc. The arc in k-space sampled by the measurement will be referred to as the detection window.

The detection window varies for each diffraction angle measured and the locus of the centres of the detection windows will be referred to as the scan path.

Preferably, measurement is done on a reflection for which the parameter $\cos(\gamma-\beta)/\cos\beta$ is less than 1, where $\gamma$ is the angle between the scan path and the z direction perpendicular to the substrate, and $\beta$ is the angle between the detection window and the x direction along the substrate in the scattering plane. Further preferably $\tan\beta$ is as small as possible.

The system may be arranged to measure the predetermined reflection by selecting the range of angles of the convergent incoming beam of x-rays to the sample surface and the range of diffraction angles ($\epsilon$) such that the region of k-space sampled by the range of diffracted beams includes the predetermined reflection.

The sample may be a structure grown on a single crystal substrate. In this case, the measurement system conveniently measures the angle between at least one diffraction peak from the structure and at least one diffraction peak from the substrate.

The X-ray diffraction system may include a moveable slit between the X-ray source and the monochromator for varying the incident angle of X-rays incident on the sample. In this way; two-dimensional scans of the scattering intensity in k-space may be carried out. Thus in this case the plurality of measurements of intensity against diffraction angle includes a sequence of measurements of intensity for different incident angles.

In another aspect, the invention relates to a deposition system with an X-ray diffraction apparatus. The system includes a growth chamber, a rotating sample stage in the growth chamber, a first X-ray window in the growth chamber, and a second X-ray window in the growth chamber. The system further includes a line X-ray source for emitting X-rays, and a Johansson monochromator for directing the X-rays emitted by the line X-ray source as a convergent monochromatic beam onto the rotating sample stage through the first X-ray window at an incident angle between the beam and the sample. A multichannel X-ray detector measures X-rays diffracted by the sample through the second X-ray window, at a plurality of diffraction angles between the diffracted X-rays and the sample surface, wherein the incident angle is greater than 45° and the diffraction angle less than 30°.

In a yet further aspect, the invention also relates to a method of measuring an X-ray diffraction pattern. The method includes mounting a sample on a sample stage, and rotating the sample stage to have a rotation period $t_r$. X-rays emitted by the line X-ray source are directed as a convergent monochromatic beam onto the rotating sample stage in the growth chamber at an incident angle to the plane of the sample. X-rays diffracted by the sample at a plurality of diffraction angles between the diffracted X-rays and the sample surface are measured using a multichannel detector, wherein the measurement time $t_m$ of each of the plurality of measurements is given by $$t_m < \frac{t_r}{4}.$$

A plurality of measurements of intensity against angle by identifying the maximum in each set of measurements, and summing the measurements together with the maxima aligned.

BRIEF DESCRIPTION OF THE DRAWINGS

For a better understanding of the invention, embodiments will now be described, purely by way of example, with reference to the accompanying drawings in which.

Note that the Figures are purely schematic and not to scale. Like or similar components are given corresponding reference numerals in different Figures.

DETAILED DESCRIPTION OF SPECIFIC EMBODIMENTS

Figure 1:
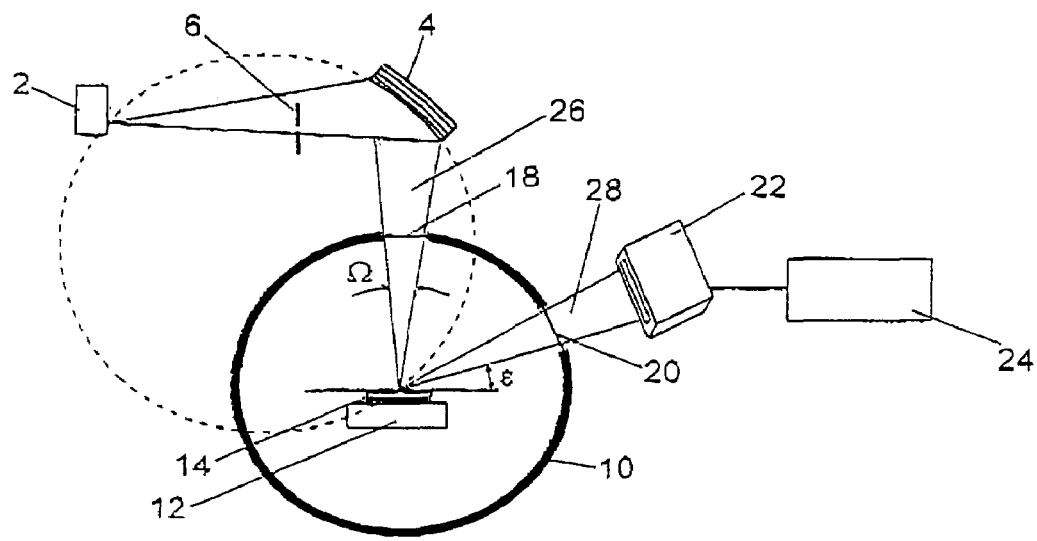
FIG. 1 shows a system according to an embodiment of the invention.

As shown in FIG. 1, in a preferred embodiment of the invention, a line source X-ray tube 2, the line extending in to the plane of the paper, is used to generate X-rays. A Johansson monochromator 4 is provided and a moveable slit 6 of adjustable size provided between the X-ray tube 2 and monochromator 4.

A growth chamber 10 has a sample stage 12 for mounting sample 14. The sample is rotated in this case by the gas flow used during growth. The growth chamber has an input window 18 for allowing X-rays from the monochromator 4 to reach the sample stage and an output window 20. In the specific example the input and exit windows are of beryllium. The windows are sealed.

A multichannel detector 22 is provided adjacent to the output window 20 for measuring X-rays passing through the output window 20. The multichannel detector 22 is connected to measurement electronics 24 for analysing the detected X-rays. The measurement electronics may contain a computer and calculation equipment for processing the data recorded on the detector 22, as will be appreciated by the skilled person.

In use, a sample 14 is mounted on the sample stage. X-rays from the X-ray source 2 pass onto monochromator 4 which directs the X-rays as a monochromatic convergent incident beam 26 onto the sample 14. The beam makes an angle δ to the plane of the sample and has a width, i.e. a range of incoming angles, of Ω. For rapid measurements, the slit 6 is omitted in order that X-rays arrive over the whole range Ω of incoming angles at once. The sample 14 diffracts the X-rays to form a diffracted beam 28 at an angle ε to the plane of the sample, the diffracted beam passing through output window 20 onto multichannel detector 22. Thus, the plane of the paper in FIG. 1 is in fact the scattering plane.

In particular, the sample 14 may be a semiconductor substrate having a thin epitaxial layer grown on the substrate in the growth chamber. The sample 14 is generally rotated during growth.

There will now follow a discussion of the geometry used since this will be needed to understand how measured results may be converted into useful data.

Figure 2:
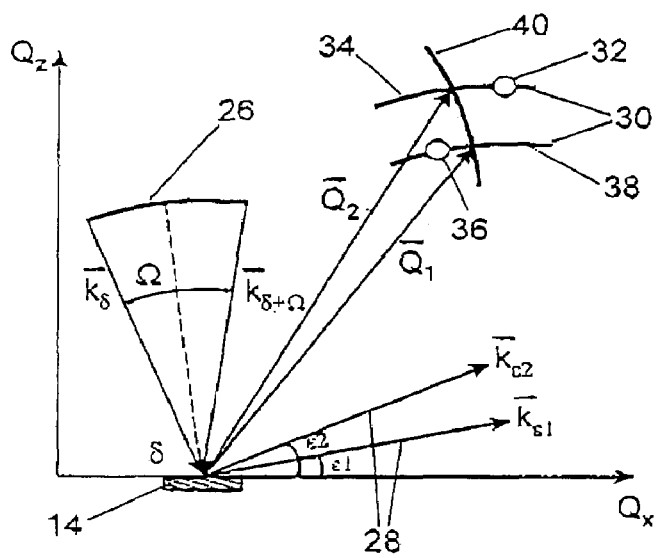
FIG. 2 shows a reciprocal space map.

FIG. 2 shows the diffraction in reciprocal (k-) space. Convergent monochromatic incident beam 26 is represented in k-space by an arc that subtends an angle Ω at the sample 14, having an angle δ with the plane of the sample. A pair of diffracted beams 28 is also shown, leaving the sample at diffraction angles $\epsilon_1$ and $\epsilon_2$. Different angles ε of diffracted beam 28 correspond to different detection windows 30.

Consider first one of these diffracted beams ($k_{\epsilon 1}$), which will be caused by reflection of the incoming X-rays which arrive at a range of angles represented by arc 26. By subtraction of vectors, the set-up samples detection window 38 in k-space, i.e. the intensity of diffracted beam 28 is dependent on the sum of k-space diffraction effects integrated over detection window 30, corresponding to the arc of the convergent monochromatic incident beam shifted by a vector $k_{\epsilon 1}$ corresponding to the diffraction angle ε and the wavelength λ of the monochromatic incident beam. A second diffracted beam ($k_{\epsilon 2}$) corresponds to another detection window 34.

The locus of the detection window 30 in k-space over different diffraction angles ε is indicated by line 40 which shows the scan path, i.e. the path of the diffraction window at different diffraction angles.

Note that the region of k-spaced spanned by the different detection windows is limited and there may be only a single or a limited number of reflections in that window from the substrate, and a limited number from the epilayer or other structure on the substrate.

Figure 3:
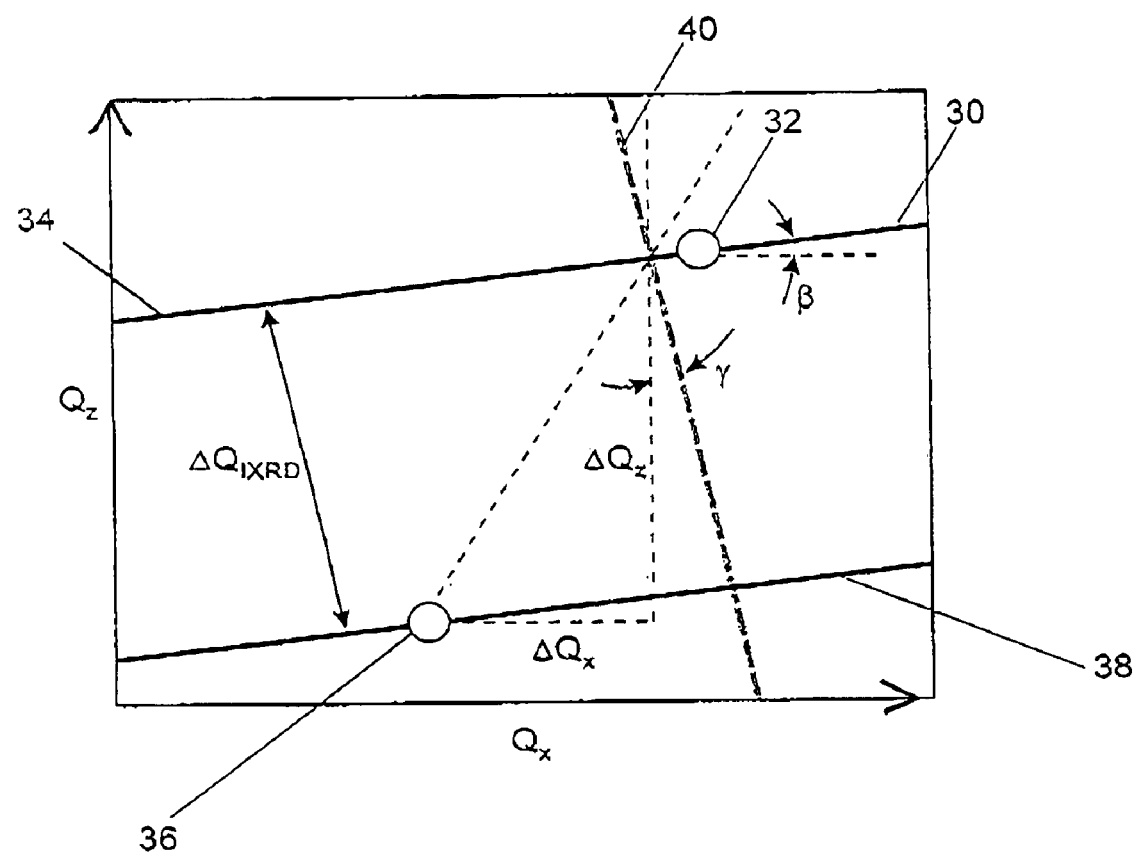
FIG. 3 shows a further reciprocal space map.
Figure 6:
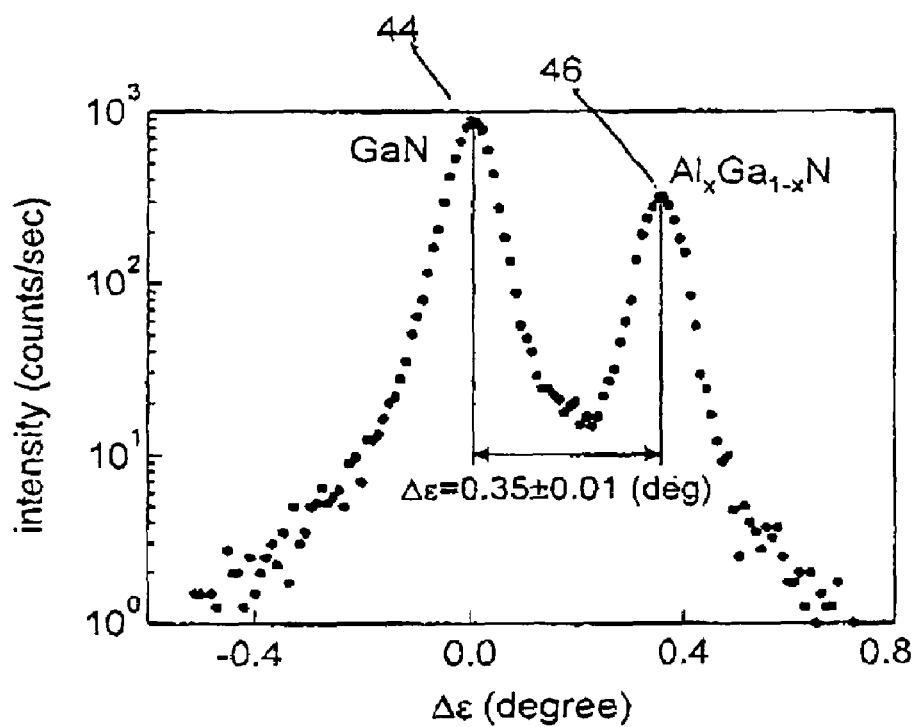
FIG. 6 shows a first set of results measured using the invention.

A detail from FIG. 2 is shown as FIG. 3 which shows in particular substrate reciprocal lattice point 32 and corresponding detection window 34 and epilayer reciprocal lattice point 36 and corresponding detection window 38. These give rise to corresponding substrate 44 and epilayer 46 peaks in the intensity measured against angle, sample results of which are shown in FIG. 6 which will be described in more detail below. The measured angle between the peaks Δε gives the distance in reciprocal space $\Delta Q_{IXRD}$ between the corresponding detection windows 34, 38 measured along the scan path 40, using formula:

$$\Delta Q_{IXRD} = \frac{2\pi}{\lambda} \Delta\varepsilon \qquad (1)$$

where λ is the wavelength of the monochromatic X-rays.

For measurement in-situ, the epilayer or layers grown on a substrate may well be fully strained on the substrate, i.e. may adopt the lateral lattice parameter of the substrate. In this case, the key measurement is the vertical lattice parameter c of the epilayer, which is directly related to the position of epilayer reflection in reciprocal space $Q_z$ (measured in the direction perpendicular to the substrate) and index of reflection by $c = 2\pi l/Q_3$, where l is the parameter 1 in the (hjkl) reflection and so l=4 for the (1124) reflection.

Since the lattice parameter of the substrate is known, the vertical position of the lattice peak is known so to find the vertical position of the epilayer reflection requires a measure of $\Delta Q_z$, the distance between substrate and epilayer reflections in reciprocal space in the direction perpendicular to the substrate.

Referring to FIG. 3, this is given by $$\Delta Q_z = \Delta Q_{IXRD} \cdot \frac{\cos(\gamma - \beta)}{\cos\beta} + \Delta Q_x \tan\beta \qquad (2)$$

where γ is the angle between the scan path 40 and the z direction perpendicular to the substrate, and β is the angle between the detection window 30 and the x direction along the substrate in the scattering plane, as shown in FIG. 3.

It is useful to pick a good reflection as substrate reciprocal lattice point 32, where "good" refers to three parameters as will now be explained. The first criterion for a good reflection is a reflection for which the parameter cos (γ−β)/cos β is less than or equal to 1 so that good resolution in $\Delta Q_z$ may be obtained.

From equation (2) it will be also noted that the results only measure one parameter $Q_{IXRD}$ and the lateral distance in reciprocal space $\Delta Q_x$ may in general not be known. In principle, this means that $\Delta Q_z$ is not exactly determined. However, this difficulty can be alleviated by picking a suitable reflection for which tan β is small, preferably less than 0.2 or further preferably 0.1, the second criterion. In this case, the value of $\Delta Q_x$ can be assumed to be zero since it does not affect $\Delta Q_z$ much. Thus, although only one parameter is measured, this gives $\Delta Q_z$.

Another variable for different reflections is the structure factor F. Accordingly, the third criterion is to pick a reflection with a relatively high structure factor F to ensure a strong diffraction.

Consider for example a substrate of h-GaN (gallium nitride). Table 1 shows possible reflections and values of these parameters for these reflections. TABLE 1

TABLE 1

|  | cos (γ − β)/cosβ | tan β | F |
| --- | --- | --- | --- |
| (2̄024) | 4.78 | 4.96 | 11.5 |
| (1̄1̄24) | 5.22 | 5.21 | 48.5 |
| (0002) | 1.91 | 3.21 | 48.5 |
| (202̄4) | 0.95 | −0.14 | 11.5 |
| (112̄4) | 0.99 | 0.02 | 24.5 |

It will be seen that by using a particular reflection (1124), good results can be achieved.

Other substrate crystals may require other reflections. Good choices include those shown in Table 2.

TABLE 2

| substrate | reflection | cos (γ − β)/cosβ | tan β | F |
| --- | --- | --- | --- | --- |
| Si | (224) | 1.02 | 0.19 | 55.8 |
| GaAs | (135) | 0.96 | 0.07 | 82.0 |
| c-GaN | (224) | 0.92 | −0.03 | 59.7 |

The skilled person will be able to calculate the parameters for various reflections for other crystals and hence determine suitable reflections for those substrates.

In general, the tan β criterion means that good reflections involve a large angle of incidence (more than 45° and preferably more than 60°, further preferably more than 75°) and a low exit angle (less than 30° and preferably less than 20°, further preferably less than 10°).

To take data, an epilayer or multi-layer structure is grown on a substrate in the growth chamber. The diffraction pattern produced by the convergent beam 26 is measured as a function of angle by multichannel detector 22. This is then converted to a value of $\Delta Q_z$ using equation 1 above. The value of this parameter gives a measure of the composition of the alloy grown. For example, in a ternary InGaN epilayer, the lattice parameter measured gives a measure of the proportion of In and Ga.

Further, where a superlattice or similar structure is grown on the substrate, the method can detect structure in the angular intensity, for example the so-called "Pendellosung fringes", that give a $\Delta Q_{IXRD}$ value. This can be converted into a $\Delta Q_z$ value using equation 1. As the skilled person will appreciate, this $\Delta Q_z$ value gives a direct measure of the superlattice periodicity as $D=2*pi/\Delta Q_z$.

In this preferred embodiment of the invention the slit 6 is not used for in-situ measurements made during growth and the complete 2° convergent beam is used for the measurements. This allows the measurement to be rapid.

As will be appreciated, the angle of convergence can be larger or smaller depending on the monochromator. This will change the spanned region in k-space.

Note that as mentioned above the sample in the growth chamber will in general be rotating, which inherently generates a wobble in the diffraction. It is a particular advantage of the invention that it can be used to measure such a rotating sample with the inherent wobble that this entails. In situ, the sample induces a wobble of about 0.3° or less, although this figure may of course vary depending on the sample stage and the accuracy with which the sample can be mounted on the sample stage. An angular spread of this order would without some countermeasure smear the measured results by this order of magnitude which could easily lose information. For example, results are presented below of a measurement of a SiGe sample with a two peaks separated by 0.17°. Such features would be swamped by the wobble of order 0.3°.

A multichannel detector is used to collect data from a single rotating and hence wobbling heterostructure. The multichannel detector detects one spectrum over a time period of 0.15 s, for a wurtzite structure rotating once a second. Several spectra are taken, and then each spectrum is shifted to align the maximum 44 of each spectrum (see FIG. 4). This is done by determining the offset in angle ε that needs to be added to the measured diffraction angles ε of each of the sets of measurements to align the maxima, adding the determined offset angle of each of the measurements in the set of measurements to the ε (x-axis) values of the set of measurement, repeating for each of the sets of measurements and then adding together the spectra.

A straightforward way of doing this is to identify the maximum in the first set of measurements, and then align each of the subsequent sets of measurements with the maximum and add the measurements together for each set of measurements in turn starting with the second.

The time 0.15 s is chosen because there are 6 (1124) symmetric reflections in one rotation of a wurzite structure. The time should ensure that only one of these reflections contributes to each measurement, and thus should be less than the rotation period 1 s/6.

More generally, if there are n symmetric reflections of the reflection being used in one rotation of the sample, and the rotation time is $t_r$, the measurement time $t_m$ should be given by $$t_m < \frac{t_r}{n} \qquad (3)$$

Figure 4:
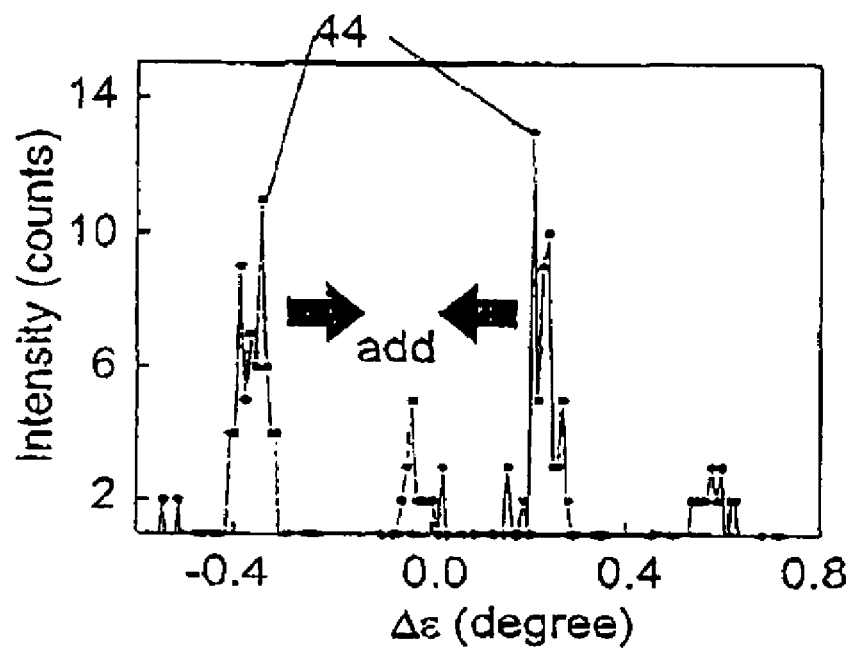
FIG. 4 shows a single spectrum obtained in a short time.
Figure 5:
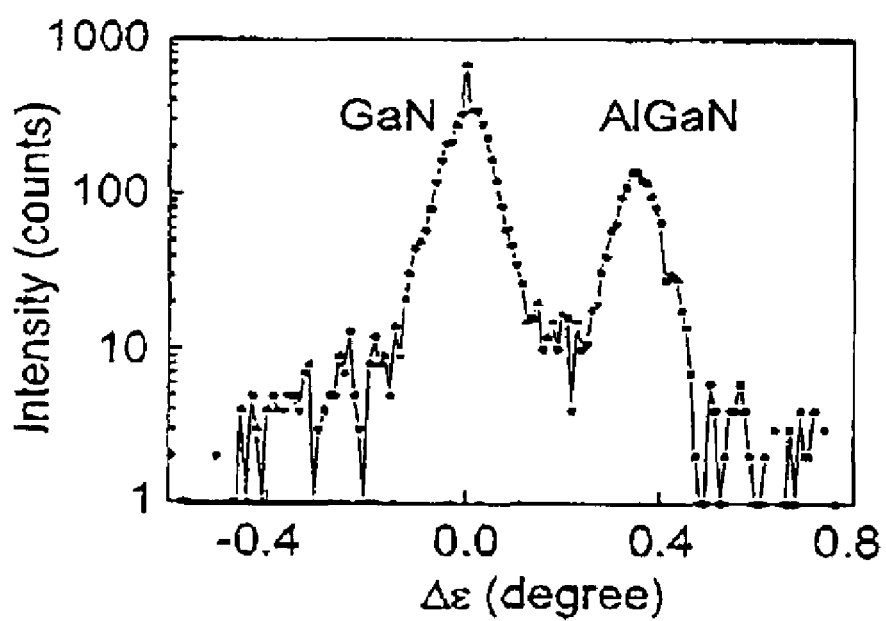
FIG. 5 shows the results of combining a number of such spectra.

FIG. 4 shows a pair of single shot spectra and FIG. 5 a combination of 100 such spectra all added together. The spectra are shifted so that peaks 44 are aligned before adding. The complete spectrum took about 100 s to measure.

By using this technique, measurements can be made in spite of the considerable wobble of the sample. This is very important in an X-ray diffraction system intended for use during growth, because it is impractical to align the sample exactly. By using the method according to the invention, possible misalignment of the sample because of the wobble becomes irrelevant.

In another embodiment of a method according to the invention, a two dimensional reciprocal space map is obtained instead of the single plot of intensity against angle obtained above.

In this case, the sample is held stationary. Slit 6 is adjusted to be narrow and tracked across the beam. In this way, the movement of the slit causes variation of the incident angle and the use of a multichannel detector allows the tracking of the diffraction intensity along the scan path. In this way a two-dimensional map of a region of k-space is built up.

Experimental results will now be described measured using a specific embodiment of apparatus according to the invention.

In the experimental set-up, the X-ray source 2 is a Cu 2.2 kW ceramic tube which is used in a line focus mode with a 0.4 mm width in the scattering plane and a 12 mm length in the direction perpendicular to the scattering plane.

The Johansson monochromator used is a 50 mm (in the curved direction) by 15 mm (in the flat direction) [111] oriented silicon monochromator crystal, using the (333) refection. Such monochromators require the line X-ray source 2, monochromator 4 and sample 14 all to lie on a notional circle known as the Rowland circle shown dotted in FIG. 1, which in this instance has a radius of 339 mm. The distance between the X-ray source 2 and the centre of the monochromator 4 and between the monochromator 4 and sample 14 is 500 mm.

Experiments showed that the convergent monochromatic beam 26 created by the monochromator 4 in this case subtends an angle Ω of about 2°.

The multichannel detector 22 was a commercially available detector of the type "PW3015/xx X'Celerator (™)" supplied by PANalytical (™).

A first example (FIG. 6) shows the spectrum of an aluminium gallium nitride ($Al_xGa_{1-x}N$) structure grown on GaN. Two peaks are clearly seen, the first corresponding to GaN and the second to $Al_xGa_{1-x}N$. The angular separation of these peaks is measured to be 0.35±0.01°. The angular resolution is that of the detector.

This gives a value for $\Delta Q_{IXRD}$ of 0.0249±0.0007 Å$^{-1}$. The vertical position of the GaN reflex for the (1124) reflection is known to be 4.8472 Å$^{-1}$.

Using equation (2) and the values of $\cos(\gamma-\beta)/\cos\beta$ from Table 1, a value for the vertical position of AlGaN reflection in reciprocal space of 4.8719 Å$^{-1}$ is obtained which corresponds in turn to a vertical lattice parameter of 5.1588±0.0008 Å. Assuming the AlGaN layer is fully strained on GaN and so shares its in-plane lattice parameter, the chemical composition x in $Al_xGa_{1-x}N$ is found to be x=0.105±0.003.

The results shown in the figure were obtained in a time scale of only 4 s. Similar results were obtained by conventional high resolution X-ray diffractometer, but this system took 30 minutes to measure the spectrum obtained using the invention in just 4 s.

Figure 7:
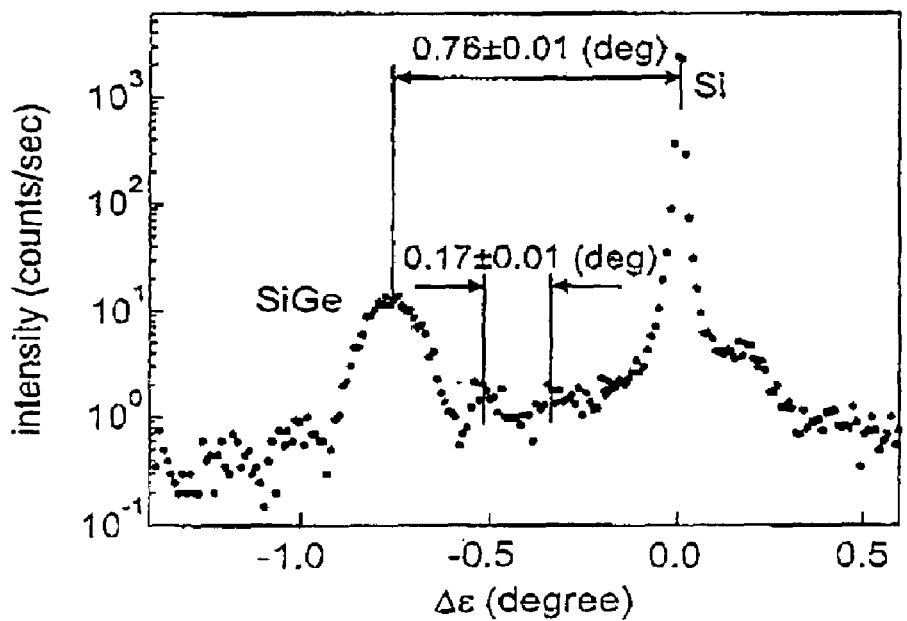
FIG. 7 shows a second set of results measured using the invention.

A second example (FIG. 7) shows a (224) spectrum of a SiGe layer grown on Si.

In this case, the calculation of the lattice parameter gives the alloy composition x to be x=0.163±0.003 for $Si_xGe_{1-x}$, using the same methods as above.

However, this example also shows Pendellosung fringes having an angular separation of 0.17±0.01°.

Using the same formulae, this gives rise to a value for $\Delta Q_z$ of 0.0123±0.0007 Å$^{-1}$ which corresponds to a layer thickness of 51±3 nm for the SiGe epilayer.

In this case, again the spectrum could be measured in 20 s using the invention compared with a time of 30 minutes for a conventional high resolution system.

Figures 8, 9:
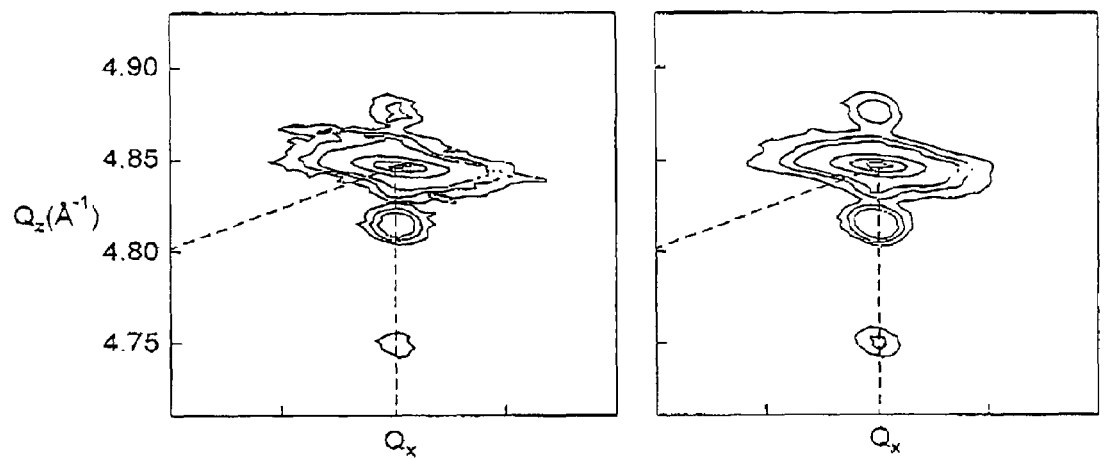
FIG. 8 shows a two-dimensional reciprocal space map using the invention.
FIG. 9 shows a comparable two-dimensional reciprocal space map obtained using conventional high-resolution diffraction.

FIG. 8 shows contours of scattered intensity measured in a two-dimensional plot on a InGaN/GaN multiple quantum wells grown on a sapphire substrate. Note in this case the main GaN peak together with multiple additional reflections caused by the superlattice. The distance of the subsidiary peaks gives the superlattice constant.

As in the previous examples, the time taken to take measurements was much less than using a conventional high resolution system. FIG. 9 illustrates results obtained using such a conventional system in 13 hours. These results are extremely similar to those obtained using the invention, shown in FIG. 8, but the measurements according to the invention took only 25 minutes.

The invention is not restricted to the embodiments discussed above and the skilled person will readily be able to adapt the invention, for example to measure different sample types or materials. The skilled person will also realise how to adapt the diffractometer to fit different kinds of deposition, growth and other systems other than the MOCVD system discussed above.

Although the invention is particularly useful for growth chambers, it may also be used for measuring rotating samples in other contexts.

What is claimed is:

1. An X-ray diffraction system, comprising:
   an X-ray source (2) for emitting X-rays;
   a rotating sample stage (12) for mounting a sample;
   control electronics for determining the rotation period of the sample stage;
   a Johansson monochromator (4) for directing the X-rays emitted by the X-ray source as a convergent monochromatic beam (26) defining a range of convergent incident angles onto the sample;
   a multichannel X-ray detector (22) arranged to make a plurality of sets of measurements of intensity with a measurement time $t_m$, each set of measurements of intensity being a set of measurements of intensity of X-rays diffracted by the sample at a plurality of diffraction angles (ε), for making measurements of intensity with a measurement time $t_m$ determined by the control electronics at $$t_m < \frac{t_r}{4}$$

where $t_r$ is the rotation period of the sample stage; and
   a measurement system (24) for combining a plurality of the sets of measurements of intensity against diffraction angle by identifying the maximum in each set of measurements, and summing the sets of measurements together with the maxima aligned, the measurement system controlled by the control electronics.

2. An X ray diffraction system according to claim 1 wherein the control electronics are adapted to set the measurement time $t_m$ for the sample to $$t_m < \frac{t_r}{n},$$

when the sample has n symmetric reflections about one axis of the sample and n is an integer at least 4.

3. An X-ray diffraction system according to claim 1 further comprising:
   a growth chamber (10), the rotating sample stage (12) contained in the growth chamber (10);
   a first X-ray window (18) in the growth chamber arranged to pass incident X-rays from the Johansson monochromator (4) to the sample; and
   a second X-ray window (20) in the growth chamber arranged to pass diffracted X-rays from the sample to the multichannel X-ray detector.

4. An X-ray diffraction system according to claim 3 wherein the incidence angles are greater than 45° and the diffraction angles less than 30°.

5. An X-ray diffraction system according to claim 4;
   wherein the system is arranged to measure a reflection of the sample for which a parameter $\cos(\gamma-\beta)/\cos\beta$ is less than 1, where γ is the angle between a scan path (40) and the z direction perpendicular to the sample, and β is an angle between a detection window (30) and the x direction along the sample in a scattering plane; the detection window (30) being the arc in k-space sampled at a single diffraction angle (ε) and the scan path (40) being a locus of the centres of the detection window (30) in k-space for different diffraction angles (ε).

6. An X-ray diffraction system according to claim 5 wherein said reflection is set by the control electronics such that tan β is less than 0.2.

7. An X-ray diffraction system according to claim 4, wherein the sample is a structure grown on a single crystal substrate, and wherein the control means measures the angle between at least one diffraction peak from the structure and at least one diffraction peak from the substrate.

8. An X-ray diffraction system according to claim 1 further comprising a moveable slit between the X-ray source and the sample for varying the angles of X-rays incident on the sample.

9. A deposition system with an X-ray diffraction apparatus, comprising:
 a growth chamber;
 a rotating sample stage in the growth chamber for mounting a sample;
 a first X-ray window in the growth chamber;
 a second X-ray window in the growth chamber;
 a line X-ray source for emitting X-rays;
 a Johansson monochromator for directing the X-rays emitted by the line X-ray source as a convergent monochromatic beam onto the sample through the first X-ray window at a range of incident angles between the beam and the sample;
 a multichannel X-ray detector for measuring X-rays diffracted by the sample through the second X-ray window, at a plurality of diffraction angles between the diffracted X-rays and the sample;
 wherein the incident angles are greater than 45° and the diffraction angles less than 30°; and a measurement system for combining a plurality of measurements of intensity against diffraction angle by identifying the maximum in each set of measurements, and summing the measurements together with the maxima aligned.

10. An X-ray diffraction system according to claim 9 further including control electronics for determining the rotation period $t_r$ of the sample stage and for determining measurement parameters, wherein;
 the multichannel detector is arranged to measure each of the plurality of measurements in a measurement time for each sample $t_m$ given by $$t_m < \frac{t_r}{n}.$$

11. A method of measuring an X-ray diffraction pattern in a growth chamber, including:
 mounting a sample on a sample stage in a growth chamber;
 rotating the sample stage to have a rotation period $t_r$;
 directing X-rays emitted by a line X-ray source as a convergent monochromatic beam onto the sample through a first X-ray window in the growth chamber at a range of incident angles to the plane of the sample;
 measuring X-rays diffracted by the sample at a plurality of diffraction angles between diffracted X-rays and the sample passing through a second X-ray window in the growth chamber using a multichannel detector, wherein the measurement time $t_m$ of each of the plurality of measurements is given by $$t_m < \frac{t_r}{4}.$$

and
 combining a plurality of measurements of intensity against diffraction angle by identifying the maximum in each set of measurements, and summing the measurements together with the maxima aligned.

12. A method according to claim 11 wherein the measurement time of each of the plurality of measurements is set to $$t_m < \frac{t_r}{n},$$

when the sample has n symmetric reflections about one axis of the sample, where n is an integer at least 4.

13. A method according to claim 11, wherein the incident angles are greater than 45° and the diffraction angles less than 30°.

* * * * *